United States Patent [19]

Matsuura

[11] Patent Number: 4,784,119

[45] Date of Patent: Nov. 15, 1988

[54] INSERTION ASSEMBLY OF AN ENDOSCOPE

[75] Inventor: Nobuyuki Matsuura, Tokyo, Japan

[73] Assignee: Olympus Optical Co., Ltd., Japan

[21] Appl. No.: 76,175

[22] Filed: Jul. 21, 1987

[30] Foreign Application Priority Data

Jul. 25, 1986 [JP] Japan .................................. 61-174794

[51] Int. Cl.$^4$ ............................................. A61B 1/06
[52] U.S. Cl. ....................................................... 128/6
[58] Field of Search ............................ 128/3, 4, 5, 6, 7

[56] References Cited

U.S. PATENT DOCUMENTS 4,146,019  3/1979  Bass et al. ................................. 128/6
4,419,987  12/1983  Ogiu .................................... 128/6 X

FOREIGN PATENT DOCUMENTS 60-63814  5/1985  Japan .
61-130201  8/1986  Japan .

*Primary Examiner*—William H. Grieb

[57] ABSTRACT

An endoscope comprising an insertion section having a distal-end unit which has a member having a plurality of through holes. An image guide has a distal end inserted in the first through hole. A first protective member surrounds and protects the distal end portion of the image guide. A light guide has a distal end inserted in the second through hole. A second protective member surrounds and protects the distal end portion of the light guide. The endoscope further comprises a fluid supply tube having a flexible main tube, a branch pipe, and two flexible sub-tubes. The main tube has a proximal end and a distal end which is fitted in the third through hole of said member. The branch pipe has three ends, the first of which is connected to the proximal end of the main tube. The two flexible sub-tubes are coupled to the second and third ends of the branch pipe, respectively. The branch pipe is located farther from the member of the distal-end unit than the proximal ends of the first and second protective members, and is thus spaced apart from the proximal ends of these protective members. Therefore, the proximal ends of the tubes protecting the image guide and the light guides are prevented from abutting against the branch pipe when the operation section is operated.

5 Claims, 2 Drawing Sheets

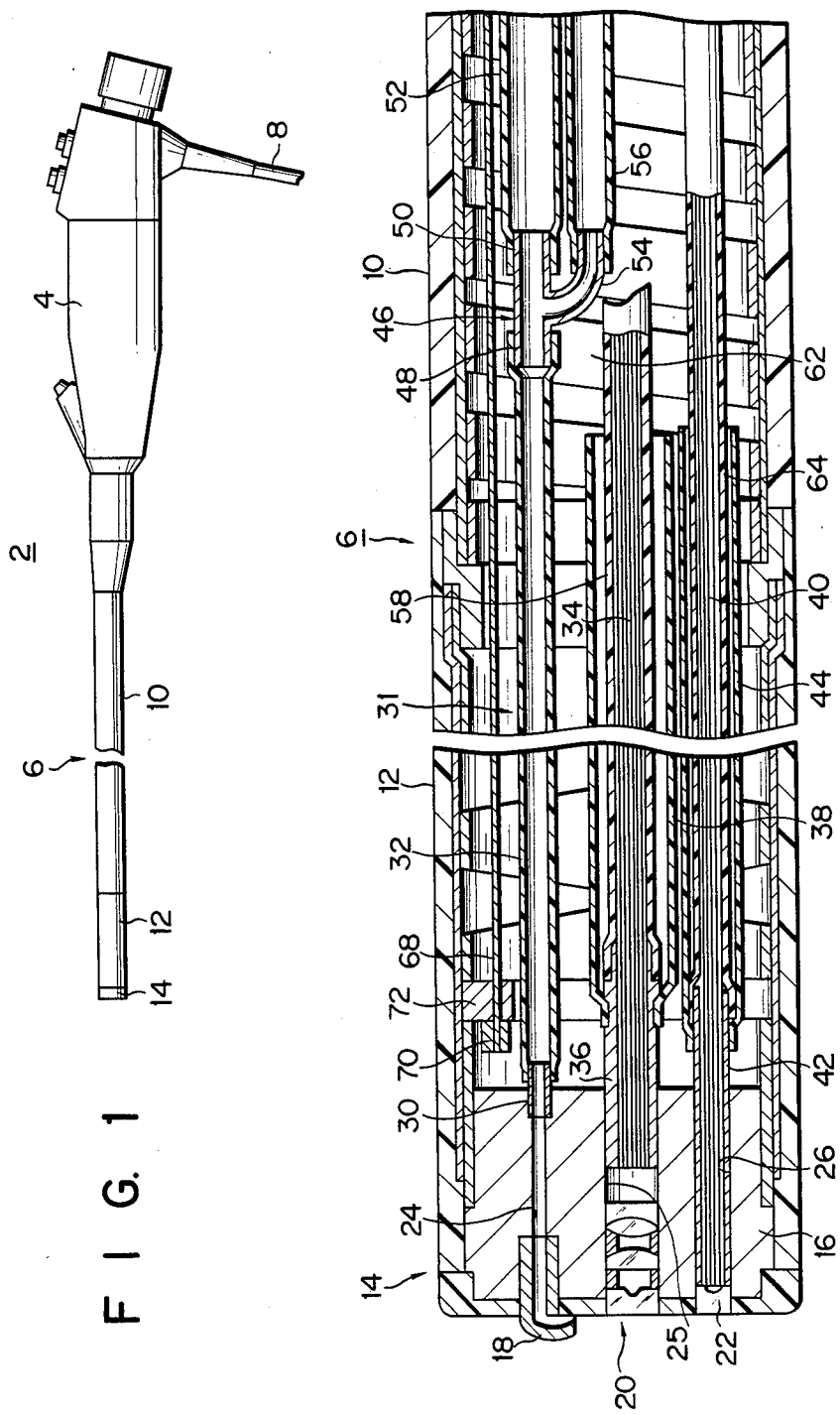

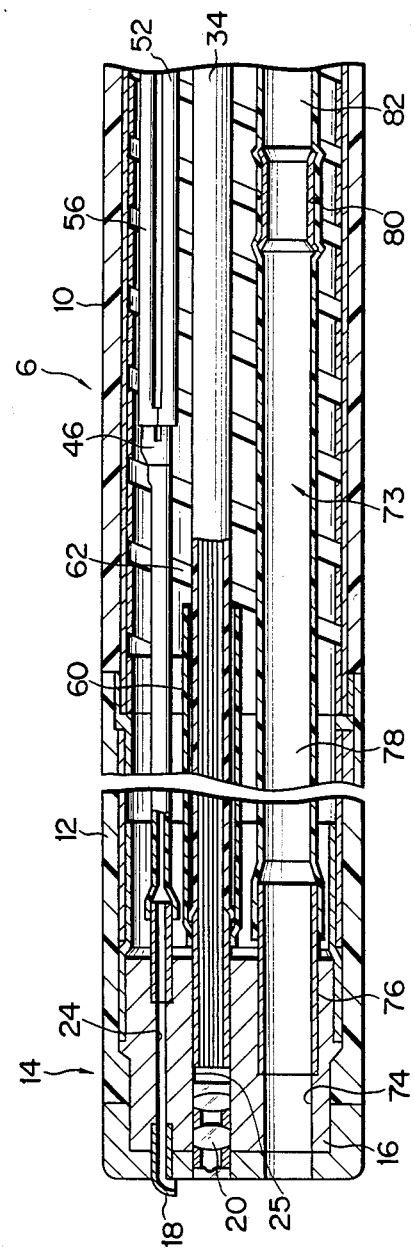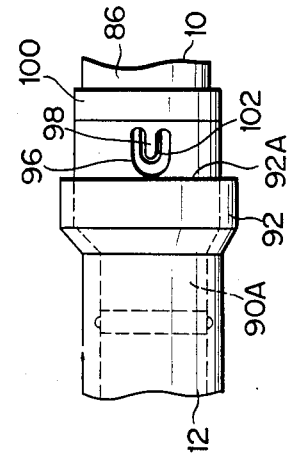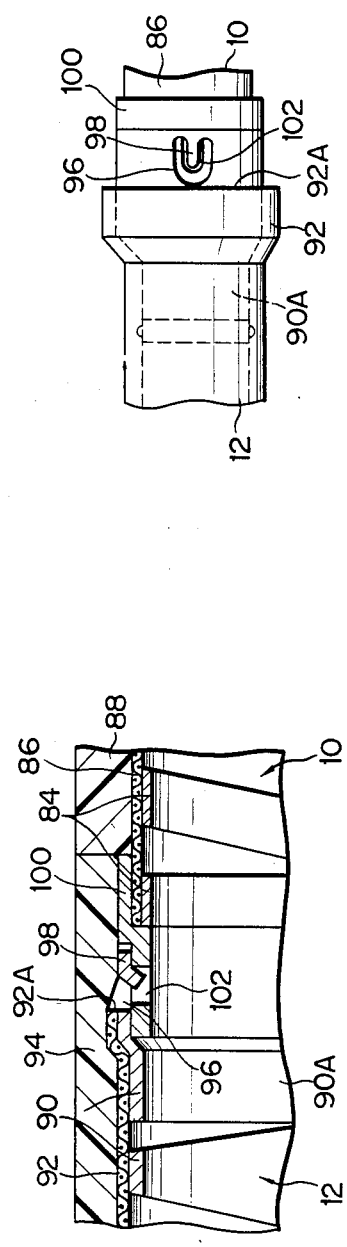

INSERTION ASSEMBLY OF AN ENDOSCOPE

BACKGROUND OF THE INVENTION

A. Field of the Invention

The present invention relates to an endoscope having a fluid supply tube with a branch section, an image guide, a light guide, and some other components.

B. Description of the Prior Art

A typical endoscope is disclosed in, for example, Japanese Patent Disclosure (KOKAI) No. 60-63814. This endoscope is provided with an operation section, an insertion section, and a light-guiding cable. The insertion section has a flexible tube, and a bendable tube, and a distal-end unit. The distal-end unit has through holes. In these holes, an air/water supply nozzle, an objective lens, an illumination lens, and the like, are accommodated. The proximal end portion of the air/water supply nozzle is fitted in the first through hole, and is connected to one end of a connection tube. The other end of the connection tube is coupled to the distal end of an air/water supply tube, which is flexible. Branch pipe is provided, which comprises two inlet portions and one outlet portion connected to the flexible tube. The proximal end of the air/water supply tube is coupled to the outlet portion of the branch pipe. The first inlet portion is coupled to a flexible, air-supply tube, and the second inlet portion is coupled to a flexible, water-supply tube.

A first connection pipe is connected to the distal end of an image guide. The first connection pipe and the objective lens are fitted in the second through hole formed in the distal-end unit. The distal end of a protective tube protecting the image guide is fastened to the first connection pipe. The protective tube is provided within the bendable tube, and its proximal end is opened.

A second connection pipe is provided within the third through hole of the distal-end unit. The illumination lens and the light guide, aligned coaxially, are fitted in one end portion of the second connection pipe. The distal end of a protective tube protecting the light guide is fastened to the second connection pipe. This protective tube is provided within the bendable tube, and its proximal end is opened.

The conventional endoscope described above has a drawback. When the operation section is operated, thus bending the bendable tube, the distal end portions of the protective tubes protecting the image guide and light guide abut against the branch pipe, inevitably bending and buckling both the image guide and the light guide. Consequently, the affected tissue or the region of interest within a body cavity cannot be seen, and a correct diagnosis cannot be made.

SUMMARY OF THE INVENTION

It is accordingly the object of this invention to provide an endoscope wherein, when the flexible tube of an insertion section is bent, the distal ends of tubes protecting an image guide and a light guide do not abut against a branch pipe connected to the flexible tube, thereby preventing the bending and buckling of the image guide and the light guide.

The above object is accomplished by an endoscope which comprises an insertion section having a distal-end unit. The distal-end unit has a member having a plurality of through holes. An image guide has a distal end inserted in the first through hole. A first protective member surrounds and protects the distal end portion of the image guide. A light guide has a distal end inserted in the second through hole. A second protective member surrounds and protects the distal end portion of the light guide. The endoscope further comprises a fluid supply tube having a flexible main tube, a branch pipe, and two flexible sub-tubes. The main tube has a proximal end and a distal end which is fitted in the third through hole of said member. The branch pipe has three ends, the first of which is connected to the proximal end of the main tube. The two flexible sub-tubes coupled to the second and third ends of the branch pipe, respectively. The branch pipe is located farther from the member of the distal-end unit than the proximal ends of the first and second protective members, and is thus spaced apart from the proximal ends of these protective members.

With the endoscope of this invention, the proximal ends of the tubes protecting the image guide and the light guides are prevented from abutting against the branch pipe when the operation section is operated, thus bending the flexible tube. The force required to bend the flexible tube is, thus, less than is required when the proximal ends of the protective tubes abut against the branch pipe. In addition, neither the image guide nor the light guide is bent or buckled when the flexible tube is bent. Therefore, an affected tissue or a region of interest, within the body cavity in which the flexible tube is inserted, can be in the view field of the endoscope.

BRIEF DESCRIPTION OF THE DRAWINGS

FIG. 1 is a side view of an endoscope according to the present invention;

FIG. 2 is a longitudinal, sectional view of the insertion section of the endoscope shown in FIG. 1;

FIG. 3 is a longitudinal, sectional view of the insertion section of another endoscope according to the present invention;

FIG. 4 is an enlarged view of that part of the insertion section shown in FIG. 3, where a flexible tube and a bendable tube are connected; and FIG. 5 is a plan view of that part of the insertion section, which is shown in FIG. 4.

DETAILED DESCRIPTION OF THE PREFERRED EMBODIMENTS

One embodiment of the present invention will now be described with reference to the accompanying drawings.

As is shown in FIG. 1, endoscope 2 according to the invention comprises operation section 4, insertion section 6, and light guide cable 8 connected to a light source (not shown). Insertion section 6 has flexible tube 10, bendable tube 12, and distal-end unit 14. Tube 12 can be bent by operating operation section 4. As is shown in FIG. 2, the main body of unit 14, or distal-end member 16, is made of hard material such as a metal. Distal-end member 16 has through holes 24, 25, and 26. Air/water supply nozzle 18 is fitted in hole 24. Objective lens 20 is fitted in hole 25 and closing the same. Illumination lens 22 is fitted in hole 26 and closing the same. Air/water supply nozzle 18 is connected to connection pipe 30 secured to distal-end member 16 by brazing or other similar means. The distal end of flexible main tube 32, which functions as air/water supply tube 31, is coupled to connection pipe 30. Branch pipe 46 is provided within insertion section 6. Branch pipe 46 has one outlet tube portion 48 and two inlet tube portions 50 and 54. The proximal end of main tube 32 is connected to outlet tube portion 48 of branch pipe 46. The distal end of a flexible sub-tube, or water-supply tube 56, is connected to tube portion 54. The distal end of another flexible sub-tube, or air-supply tube 52, is connected to tube portion 50.

First connection pipe 36, which is coupled to the distal end of image guide 34, is connected to the proximal end of member 16 and communicates with through hole 25 accommodating objective lens 20. The distal end of protective tube 38 protecting image guide 34 is coupled to the proximal end of first connection pipe 36. Protective tube 38 is provided within bendable tube 12, and its proximal end is opened.

Second connection pipe 42, which is coupled to the distal end of light guide 40, is connected to the proximal end of member 16 and communicates with through hole 26 accommodating illumination lens 22. The distal end of protective tube 44 protecting light guide 40 is coupled to the proximal end of second connection pipe 42. Protective tube 44 is also provided within bendable tube 12, and its proximal end is opened.

As is illustrated in FIG. 2, the outer periphery of image guide 34 is sheathed in outer tube 58 made of, for example, silicone rubber. The distal end of outer tube 58 is connected to first connection pipe 36. The distal end portion of outer tube 58 is sheathed in protective tube 38 for image guide 34. The proximal end of protective tube 38 is located closer to distal-end member 16 than branch pipe 46. Void space 62 is provided between tube 38 and pipe 46.

Light guide 40 is sheathed in outer tube 64 made of, for example, silicone rubber. The distal end of outer tube 64 is connected to second connection pipe 36. The distal end portion of outer tube 64 is sheathed in protective tube 44 for light guide 40. The proximal end of protective tube 44 is located closer to distal-end member 16 than branch pipe 46. Void space 62 is provided between tube 44 and pipe 46.

Bendable tube 12 can be bent by rotating a knob (not shown) provided on operation section 4 and coupled to operation wire 68 extending through flexible tube 10 and connected, at its distal end, to the inner periphery of bendable tube 12. More specifically, the proximal end of wire 68 is fastened to the knob, and the distal end thereof is connected by swaging to metal chip 70 which, in turn, is secured to projection 72 fixed to the inner periphery of the distal end portion of bendable tube 12. Alternatively, a ball shaped chip may be formed by plasma heating at the distal end of wire 68.

Since void space 62 is provided between branch pipe 46, on the one hand, and protective tubes 38 and 44, on the other, the proximal ends of tubes 38 and 44 do not abut against branch pipe 46 when tubes 38 and 44 are moved rearwardly as bendable tube 12 is bent. Hence, neither image guide 34 nor light guide 40 is bent or buckled.

A second embodiment of the present invention will now be described with reference to FIGS. 3 to 5. This endoscope also has insertion section 6. As is shown in FIG. 3, forceps channel 73 is arranged in insertion section 6. Channel 73 is used not only to guide a forceps or similar medical instruments into a body cavity, but also to draw out filth from the body cavity under suction force. Insertion section 6 has distal-end unit 14. The main body of unit 14, or distal-end member 16 has through hole 74. Connection pipe 76 is connected to the proximal end of member 16 and communicates with through hole 74. The proximal end of connection pipe 76 is coupled to the distal end of relatively flexible tube 78. The proximal end of tube 78 is connected to the distal end of relatively rigid tube 82 by coupling 80. Coupling 80 is located at the rear of branch pipe 46. Branch pipe 46 has two inlet tube portions connected to air-supply tube 52 and water-supply tube 56, respectively.

As is shown in FIG. 4, the flex 84 of flexible tube 10 is sheathed in tubular blade 86. The outer periphery of blade 86 is coated with synthetic resin 88. Bendable tube 12 is provided in insertion section 6. Bendable tube 12 comprises a plurality of cylindrical segments 90 rotatably connected in series, thus forming a hollow cylinder. This hollow cylinder is sheathed in flexible tubular blade 92. The outer periphery of blade 92 is sheathed in elastic tubular member 94 made of rubber or the like.

Bendable tube 12 is secured to flexible tube 10 in the following way. The rearmost segment 90A of tube 12 has U-shaped holes 96 arranged equidistantly in the circumferential direction. These holes 96 have been made by punching or laser-beam cutting. Each U-shaped hole 96 defines projection 98. Cylindrical cap 100 is attached to the distal end of flexible tube 10. Holes 102 are cut in cap 100 and spaced apart in the circumferential direction of the cap 100. Cap 100 is positioned such that holes 102 are aligned with projections 96 of segment 90A. Projections 98 are then bent inwardly into holes 102, whereby bendable tube 12 is fastened to flexible tube 10.

Proximal end 92A of blade 92 covering the outer periphery of the hollow cylinder is located nearer distal-end unit 14 than projections 98 of rearmost segment 90A.

In the second embodiment, since coupling 80 is located closer to operation section 4 than branch pipe 46, tube 10 is relatively thin. Relatively flexible tube 78 provided within tube 12 renders it easy to operate tube 12. Further, relatively rigid tube 82, which is connected to the proximal end of tube 78 reinforces the forceps channel. Still further, the use of segment 90A having projections 98 and cap 100 having holes 102 makes it easy to fasten flexible tube 10 and bendable tube 12 firmly together.

The present invention is not limited to the first and second embodiments. For instance, void space 62 can be provided at the rear of only protective tube 38 protecting the image guide, or protective tube 44 protecting the light guide, whichever closer to branch pipe 46, not at the rear of both protective tubes as in the embodiment described above.

What is claimed is:
1. An endoscope having an insertion section with a distal-end unit, comprising:
  a distal-end member provided within said distal-end unit and having first, second, third and fourth through holes;
  an image guide having a distal end inserted in the first through hole;
  a first protective member having a distal end and a proximal end, and surrounding and protecting the distal end portion of said image guide;
  a light guide having a distal end inserted in the second through hole;

a second protective member having a distal end and a proximal end, and surrounding and protecting the distal end portion of said light guide; and a fluid supply tube having:

a main tube having a distal end inserted in the third through hole of said distal-end member, and a proximal end;

a branch pipe having first end coupled to the proximal end of said main tube, second and third ends, and located farther from said distal-end member than from the proximal end of at least one of said protective members, and spaced apart from the proximal end of said protective member for a predetermined distance;

at least two flexible sub-tubes coupled to the second and third ends of the branch pipe, respectively.

2. The endoscope according to claim 1, wherein said branch pipe is located farther from said distal-end member than from the proximal ends of said first and second protective members, and is spaced apart from the proximal ends of said first and second protective members for a predetermined distance.

3. The endoscope according to claim 1, further comprising a forceps channel which has:

a relatively flexible tube having a distal end inserted in the fourth through hole of said distal-end member, and a proximal end;

a coupling member connected to the proximal end of said tube and located farther from said distal-end member than from said branch pipe; and a relatively rigid tube connected to said coupling member.

4. The endoscope according to, claim 1, wherein said insertion section has a bendable tube connected to said distal-end member, and a flexible tube connected to the bendable tube by coupling means.

5. The endoscope according to claim 4, wherein said bendable tube comprises a plurality of segments, and said coupling means comprises projections integrally formed with the rearmost segment and holes cut in a cap attached to the distal end of said flexible tube.

* * * * *